US006226873B1

(12) United States Patent
Okumura

(10) Patent No.: US 6,226,873 B1
(45) Date of Patent: May 8, 2001

(54) CUTTER KNIFE

(75) Inventor: Kazuyoshi Okumura, Kyoto (JP)

(73) Assignee: Kyoto Doki, K.K., Kyoto (JP)

( * ) Notice: Subject to any disclaimer, the term of this patent is extended or adjusted under 35 U.S.C. 154(b) by 0 days.

(21) Appl. No.: 09/271,730

(22) Filed: Mar. 18, 1999

(30) Foreign Application Priority Data

Mar. 20, 1998 (JP) ..................... 10-071664

(51) Int. Cl.[7] ..................... A61B 17/32
(52) U.S. Cl. ..................... 30/162; 30/335
(58) Field of Search ..................... 30/162, 335, 336, 30/337, 329

(56) References Cited

U.S. PATENT DOCUMENTS

| | | | |
|---|---|---|---|
| D. 313,540 | 1/1991 | Sauber | D8/98 |
| D. 345,290 | 3/1994 | Okada | D8/107 |
| D. 354,900 | 1/1995 | Toor et al. | D8/99 |
| D. 386,959 | 12/1997 | Hirai | D8/99 |
| 4,170,062 * | 10/1979 | Machida | 30/162 |
| 4,320,576 | 3/1982 | Beermann | 30/162 |
| 4,322,885 | 4/1982 | Osada | 30/162 |
| 4,361,958 | 12/1982 | Gilbert | 30/162 |
| 4,524,518 | 6/1985 | West | 30/330 |
| 4,586,256 | 5/1986 | Weimann | 30/162 |
| 4,615,118 | 10/1986 | Ihata | 30/151 |
| 4,663,845 | 5/1987 | Weimann | 30/162 |
| 4,897,920 | 2/1990 | Dunbar | 30/90.4 |
| 4,899,443 | 2/1990 | Beermann | 30/162 |
| 4,930,218 | 6/1990 | Jacoff | 30/162 |
| 5,012,581 | 5/1991 | Fletcher et al. | 30/162 |
| 5,086,562 | 2/1992 | Jacoff | 30/162 |
| 5,121,544 | 6/1992 | Gilbert | 30/162 |
| 5,203,085 | 4/1993 | Berns | 30/163 |
| 5,269,063 | 12/1993 | Okada | 30/162 |
| 5,299,355 | 4/1994 | Boda | 30/162 |
| 5,301,428 | 4/1994 | Wilcox | 30/162 |
| 5,495,670 | 3/1996 | Quinn | 30/162 |
| 5,497,553 | 3/1996 | Chong | 30/162 |
| 5,502,896 | 4/1996 | Chen | 30/162 |
| 5,531,754 * | 7/1996 | Shackelford, Sr. et al. | 30/162 X |
| 5,581,890 | 12/1996 | Schmidt | 30/162 |
| 5,613,300 | 3/1997 | Schmidt | 30/2 |
| 5,711,077 | 1/1998 | Schulz et al. | 30/160 |

FOREIGN PATENT DOCUMENTS

| | | | |
|---|---|---|---|
| 406327849 * | 11/1994 | (JP) | 30/162 |

* cited by examiner

*Primary Examiner*—Rinaldi I. Rada
(74) *Attorney, Agent, or Firm*—Davis Wright Tremaine LLP

(57) ABSTRACT

To provide a cutter knife which can be stepwise automatically locked while preventing a leaf spring from being unusably deformed. A holder 1 has engaging recesses 1*b* of an isosceles trapezoid formed in its upper face, and a slider is so inserted in a slide groove as to move back and forth. In a center recess 2*g* formed in a body member 2 of the slider, there is inserted a leaf spring 4. In an opening 2*d* into and out of which the protruding portion of the leaf spring 4 is to go, there is disposed a boss 2*e* which is erected on the body member to regulating the movement of the leaf spring. An operation member 3, as movably supported by the body member, is provided with an engaging groove 3*b* and a movable stopper 3*c*. As the operation member is moved forward or backward, the movable stopper allows the backward movement of the protruding portion, and the engaging groove can depress the protruding portion of the leaf spring out of engagement from the engaging recess so that the slider can be moved.

8 Claims, 3 Drawing Sheets

CUTTER KNIFE

TECHNICAL FIELD OF THE INVENTION

The present invention relates to an automatic locking type cutter knife.

BACKGROUND OF THE INVENTION

The present invention relates to an automatic locking type cutter knife. The automatic locking type cutter knife is known to have a variety of operations and structures. The automatic locking type cutter knife, as disclosed in Examined Published Japanese Utility Model Application No. 57-54771 or 61-35177, is equipped with a stopper mounted on the back face of the center protruding portion of a retaining leaf spring for preventing the leaf spring from turning. This structure can prevent the turning of the leaf spring when the stopper is moved in one direction. When the spring is released, it is troublesome to return the stopper. When a force acts to move a slider to be coupled to a cutter blade while the slider is being retained by the stopper, the center protruding portion of the leaf spring is pushed forward or backward onto the square hole of a blade holder. As a result, the center protruding portion of the leaf spring is pushed so much between the square hole and the corrugated ridge of the knife frame that it is unusably deformed.

On the other hand, an automatic locking type cutter knife, as disclosed in Unexamined Published Japanese Patent Application No. 6-327849, employs a leaf spring having a generally triangular projecting portion for a triangular engaging groove. This structure raises a problem in the reliability of the retaining force of the cutter blade. Another problem is that the leaf spring is liable to come out from the opening of a center recess, as formed in a body member of the slider, and to be deformed.

In an automatic locking type cutter knife, as disclosed in Examined Published Japanese Patent Application No. 7-85752, a leaf spring is provided with a flat spring portion extending in the forward direction of a cutter blade, and a protruding portion having an inverted U-shaped section and protruding at a right angle with respect to the spring portion. This structure has a problem that the force to be applied by the leaf spring to an engaging groove is weak in a neutral position.

The invention has been conceived with a view to the background thus far described and has an object to provide a cutter knife which can be stepwise automatically locked while preventing the leaf spring from being unusably deformed.

SUMMARY OF THE INVENTION

According to an embodiment of the invention there is provided a cutter knife comprising: a holder having a plurality of engaging recesses of an isosceles trapezoid shape formed intermittently in its upper face to have a larger width outward and a slide groove into which a cutter blade is to be inserted movably back and forth; a slider inserted in the slide groove of said holder and formed to mount said cutter blade thereon; and a leaf spring member supported by said slider to come into and out of engagement with said engaging recesses, characterized: in that said slider includes a body member, an operation member supported movably on said body member, and a leaf spring member; in that said leaf spring member includes leg portions expanded obliquely, a protruding portion of an isosceles trapezoid formed at the center portion of said leg portions and capable of engaging with said engaging recesses, and a wide portion formed in the vicinity of the root portion of said protruding portion and made wider than said obliquely expanded leg portions; in that said body member includes a center recess, an opening formed at the center in the upper face of said center recess for allowing the protruding portion of said leaf spring to go into and out of it, and a boss positioned in the vicinity of said opening for preventing the deformation of the protruding portion of said leaf spring; and in that said operation member includes a movable stopper for engaging with said wide portion at its neutral position to prevent the protruding portion of said leaf spring from moving backward, and an engaging groove for pushing downward said protruding portion against the elasticity of said leaf spring by the moving operation of said operation member so that the protruding portion of said leaf spring may be released from said engaging recesses.

BRIEF DESCRIPTION OF THE DRAWINGS

1. FIG. 1(A) is a top plan view, and FIG. 1 (B) is a side elevation.

2.

3.

4. FIG. 4 shows the leaf spring.

5.

DETAILED DESCRIPTION OF THE INVENTION

Figure 1A:
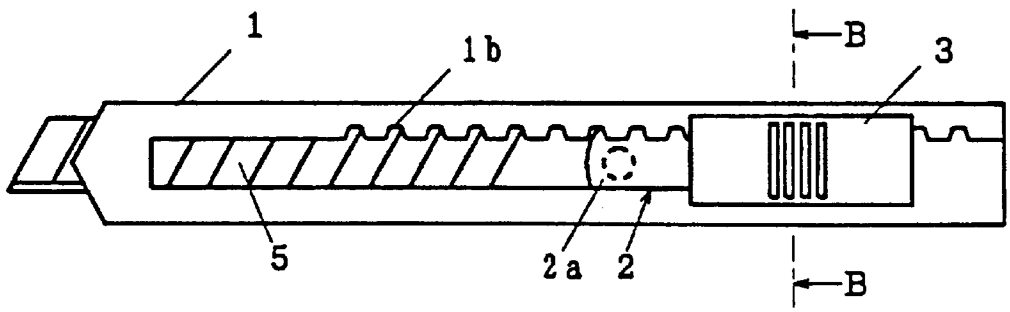
FIGS. 1(A)–(B) shows one embodiment of the cutter knife of the invention.
Figure 1B:
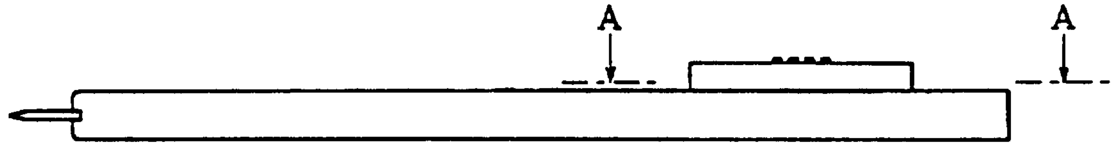

FIGS. 1(A)–(B) show one embodiment of a cutter knife of the invention, and FIG. 1(A) is a top plan view whereas FIG. 1 (B) is a side elevation. In these Figures: reference numeral 1 designates a holder; numeral 1*b* engaging recesses; numeral 2 a body member; numeral 2*a* a base plate; numeral 3 an operation member; and numeral 5 a cutter blade.

The holder 1 is a molding of a synthetic resin, but may be made of a suitable material at its partial or entire portion, such as the portion in which the engaging recesses 1*b* are formed. However, the construction, in which the entirety of the holder 1 is made of the synthetic resin as in this embodiment, is advantageous in that it can reduce the number of parts and can be produced at a low cost. In the holder 1, there is formed a slide groove in which a number of engaging recesses 1*b* are formed at one edge portion of the opening in its upper face. These engaging recesses 1*b* are formed to have a shape of an isosceles trapezoid opened outward. The angle of inclination of the sides corresponding to the legs of the isosceles trapezoids is suitable within a range of 50 degrees to 85 degrees. In the slide groove of the holder 1 there is so inserted the slider as to move back and forth. This slider is assembled of three members of the body member 2, the operation member 3 and a leaf spring and can be moved to carry a cutter blade, mounted on the body member 2, back and forth. The movement of the slider can be effected by pushing the operation member 3 forward or backward, as will be described hereinafter.

Figure 2:
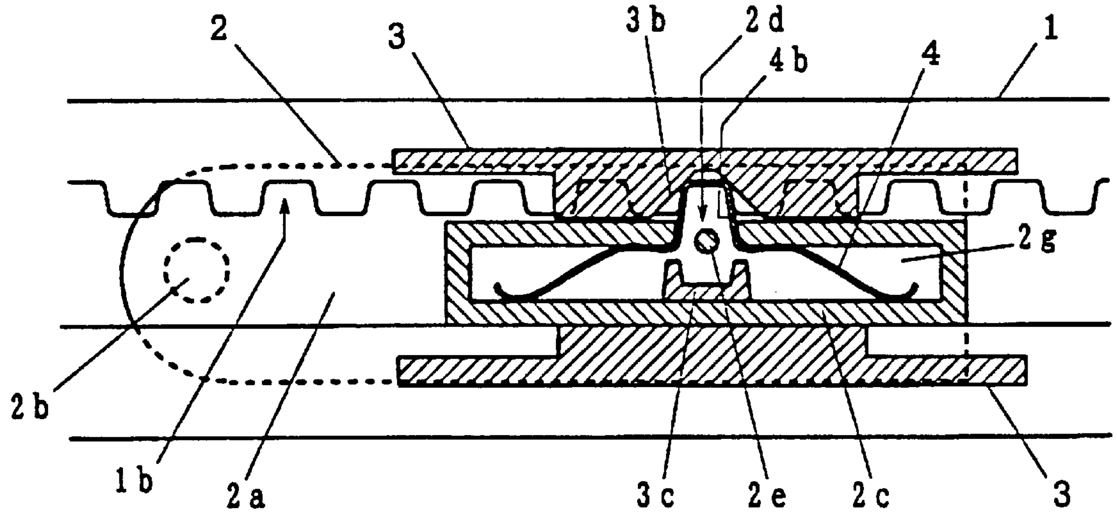
FIG. 2 shows a section taken along line A—A of FIG. 1(B).
Figure 3:
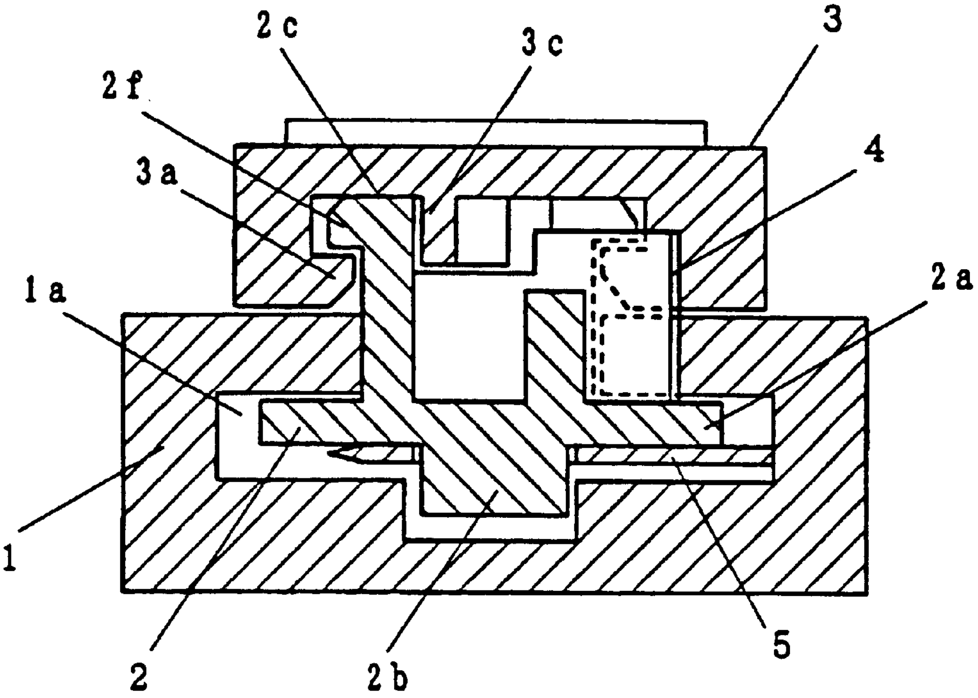
FIG. 3 shows a section taken along line B—B of FIG. 1(A).
Figure 4A:
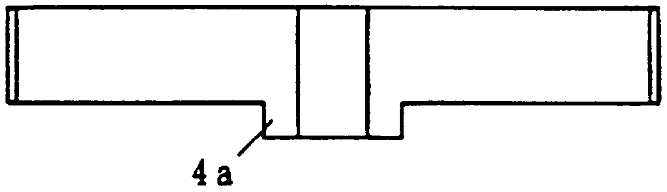
FIG. 4(A) is a top plan view.
Figure 4B:
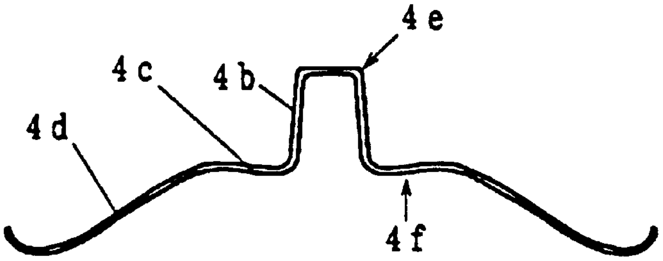
FIG. 4(B) is a side elevation.

The detail of the slider will be described with reference to FIGS. 2 to 4. FIG. 2 is a section taken along line A—A of FIG. 1(B); FIG. 3 is a section taken along line B—B of FIG. 1(A); FIG. 4(A) is a top plan view of the leaf spring; and FIG. 4(B) is a side elevation of the leaf spring. In these Figures, the description of the same portions as those of FIG. 1A will be omitted by designating them by the common reference numerals. Reference numeral 1*a* designates a slide groove; numeral 2*b* a mounting pin; numeral 2*c* an operation member supporting portion; numeral 2*d* an opening; numeral 2*e* a boss; numeral 2*f* a projecting portion; numeral 2*g* a center recess; numeral 3*a* a projecting portion; numeral 3*b* an engaging groove; numeral 3*c* a movable stopper; numeral 4 a leaf spring; numeral 4*a* a wide portion; numeral 4*b* a protruding portion; numeral 4*c* intermediate portions; numeral 4*d* leg portions; numeral 4*e* an engaging angular portion; and numeral 4*f* a back face.

The body member 2 includes: the mounting pin 2*b* for mounting the cutter blade on the side of the leading end portion of the flat base plate 2*a;* the center recess 2*g* for housing the leaf spring 4; and the operation member supporting portion 2*c*. The mounting 2*b* is fitted in the not-shown mounting hole of the cutter blade to joint the cutter blade to the slider body portion 2. The center recess 2*g* is formed into such a box shape as to rise from the slider body portion 2. In the vicinity of the center of one longitudinal side wall of the center recess 2*g,* there is formed the opening 2*d,* under which there is erected the boss 2*e*. This boss 2*e* plays a role as a stopper for regulating the moving range of the protruding portion 4*b* so as to prevent a deformation in which the protruding portion 4*b* of the leaf spring 4 could otherwise become unused. Moreover, the protruding portion 4*b* can be prevented from coming out from the opening 2*d,* thereby to hold the spring member 4 reliably in position.

As shown in FIG. 4(A), the leaf spring 4 is a flat elastic member made of phosphor bronze, for example, and is made wider at its center portion than its righthand and lefthand sides to form the wide portion 4*a*. This leaf spring 4 is shaped, as shown in FIG. 4(B), to have the protruding portion 4*b* at the center, the intermediate portions 4*c* extended rightward and leftward generally at a right angle from the protruding portion 4*b,* and the leg portions 4*d* formed on the two sides of the intermediate portions 4*c* and extended obliquely rightward and leftward. These leg portions 4*d* mainly serve to generate the spring force. The protruding portion 4*b* and the portions, as extended from the former, of the intermediate portions 4*c* are formed into the wide portion 4*a,* as shown in FIG. 4(A). Here, the shape of the leaf spring 4 is one example, and the intermediate portions 4*c* may be made so shorter than those shown in FIG. 4(B) that the wider portion 4*a* may contain the intermediate portions 4*c* entirely. Moreover, the intermediate portions 4*c* may be so eliminated that the leg portions 4*d* may be extended directly from the protruding portion 4*b.* In this modification, the wider portion 4*a* may contain so much as to contain the leg portions 4*d* partially. Since the protruding portion 4*b* is provided for engaging with the engaging recess, as will be described hereinafter, it could be said sufficient that the protruding portion 4*b* is provided with the leg portions having the spring force, and that the wide portion 4*a* forms the portion to engage with the movable stopper thereby to prevent the backward movement of the protruding portion 4*b.*

Reverting to FIGS. 2 and 3, the description will be made. In the opening 2*d* in the side wall of the center recess 2*g* formed in the body member 2 of the slider, there is so arranged the leaf spring 4 toward the engaging groove 3*b* of the operation member 3 as can move to and away from the outside.

The operation member supporting portion 2*c* supports the operation member 3 such that the operation member 3 can moved back and forth (in the moving directions of the cutter blade), and mounts the operation member 3 on the body member 2 by holding the outward projecting portion 2*f* and the inward projecting portion 3*a* of the operation member 3 in engagement with each other.

The operation member 3 is slidably supported by its supporting portion 2*c* of the body member 2 and is so positioned in a neutral state that the center of the angular engaging groove 3*b* rides on the protruding portion 4*b* of the leaf spring 4. The operation member 3 can moved back and forth across that position. The movement is limited within a predetermined range by the step portion which is formed by recessing the side faces of the operation member supporting portion 2*c*. The limiting mechanism should not be restricted thereto but could be modified to either a suitable retaining mechanism such as a stopper for limiting the forward and backward movements of the operation member 3 with respect to the body member 2 or a limiting mechanism for limiting the movements, although the modification is not shown.

The movable stopper 3*c,* as protruded from the inside of the operation member 3, can be moved by the operation member 3 with respect to the protruding portion 4*b,* and is positioned at the back of the leaf spring 4 in the center recess 2*g* of the body member 2. When the operation member 3 is in the neutral position, the crests, as protruded from the two sides of the movable stopper 3*c* of the operation member 3, are positioned at the back face 4*f* (as shown in FIG. 4) of the intermediate portions of the wide portions 4*a* of the protruding portion 4*b* of the leaf spring 4 so that they prevent the protruding portion 4*b* from moving backward and from coming out from the engaging recess 4*b* of the leaf spring 4 along the slopes of the engaging recess 1*b* of the holder 1. As a result, even if a force is applied to the edge of the cutter blade, the protruding portion 4*b* of the leaf spring 4 keeps biting the engaging recess 1*b* to prevent the cutter blade from moving back.

Figure 5:
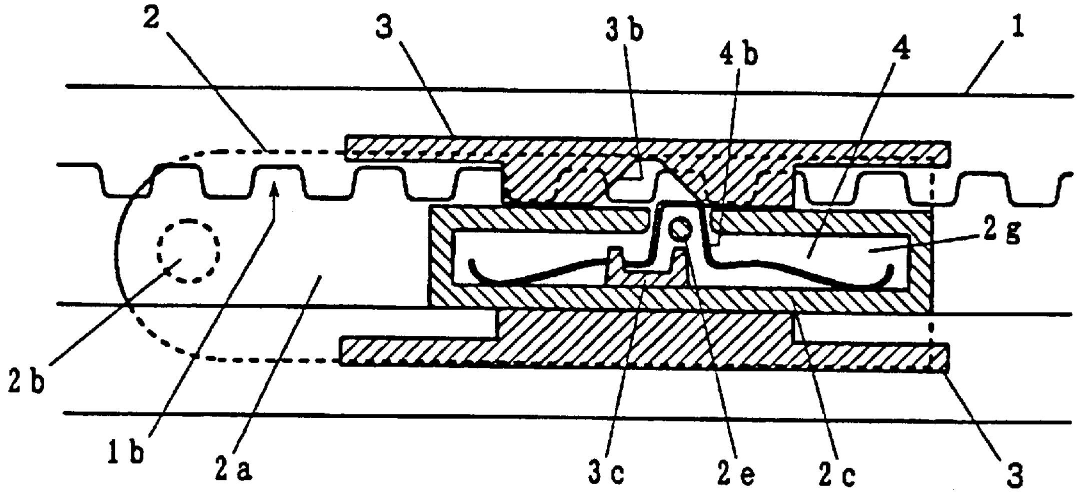
FIG. 5 shows a section taken along line A—A of FIG. 1 (B) and showing the state in which the operation member is moved forward.

In order to move the cutter, the operation member 3 is manually moved in the moving direction. This state is shown in FIG. 5. In FIG. 5, the operation member 3 is moved forward (i.e., leftward, as shown, to extract the cutter blade). Then, the leaf spring 4 is moved downward, as shown, at its engaging angular portion 4*e* (as shown in FIG. 4) against the elastic force of the leaf spring 4 by the slope of the engaging groove 3*b* of the operation member 3. Since the crests of the movable stopper 3*c* of the operation member 3 have been moved forward till them, they are positioned not to retain the wide portion 4*a* thereby to allow the backward movement of the protruding portion 4*b* so that the protruding portion 4*b* of the leaf spring 4 is pushed into the center recess 2*g* of the body member 2 to come out from the engaging recess 1*b* of the holder 1.

As the operation member 3 comes out from the engaging recess 1*b* of the protruding portion 4*b,* it can be further moved leftward so that the slider can be moved to a desired position. By releasing the operation member 3 after the movement to the desired position, the protruding portion 4*b* is returned to the position of FIG. 2 by the elasticity of the leg portions 4*d* so that the slider can be held in the locked state.

By the returns of the leg portions 4*d,* the engaging angular portion 4*e* abuts against the slop of the engaging groove 3*b* so that the operation member 3 can be returned to the initial neutral position. When the slider is to be moved backward (rightward, as shown, to return the cutter blade) of the direction of the foregoing description, the operation member 3 is moved rightward, as shown. As a result, the engaging angular portion 4*e* is pushed downward, as shown, against the elastic force of the leg portions 4*d* by the lefthand slope of the engaging groove 3*b*, and the protruding portion 4*b* can also be brought from the engaging recess 1*b* so that the slider can be moved backward by further moving the operation member 3 rightward.

As apparent from the description thus far made, according to the invention, the automatic locking can be achieved by the movable stopper which can be moved together with the operation member. There is another effect that the deformation of the protruding portion of the leaf spring can be prevented by the boss which is mounted on the body member.

I claim:

1. A cutter knife comprising:

(a) a holder having a plurality of engaging recesses of an isosceles trapezoid shape formed intermittently in its upper face and a slide groove into which a cutter blade is to be inserted movably back and forth; and (b) a leaf spring member supported by a slider to come into and out of engagement with said engaging recesses, wherein said leaf spring member includes leg portions expanded obliquely, a protruding portion of an isosceles trapezoid formed at the center portion of said leg portions and capable of engaging with said engaging recesses, and a wide portion formed at a base of said protruding portion and made wider than said obliquely expanded leg portions;

wherein the slider is inserted in the slide groove of said holder and formed to mount said cutter blade thereon and support said leaf spring, the slider comprising a body member, a boss member, and an operation member supported movably on said body member, wherein said operation member includes a movable stopper for engaging with said wide portions of the leaf spring to prevent the protruding portion of said leaf spring from moving backward when the leaf spring deflects, and an engaging groove for pushing downward said protruding portion against the elasticity of said leaf spring by the moving operation of said operation member so that the protruding portion of said leaf spring may be released from said engaging recesses.

2. The apparatus of claim 1 wherein said body member includes a center recess, an opening formed at the center in the upper face of said center recess for allowing the protruding portion of said leaf spring to go into and out of it, and a boss positioned adjacent to said opening for preventing the deformation of the protruding portion of said leaf spring.

3. A cutter knife comprising:

(a) a holder having a plurality of engaging recesses of an isosceles trapezoid shape formed intermittently in its upper face and a slide groove into which a cutter blade is to be inserted movably back and forth.

(b) a slider inserted in the slide groove of said holder and formed to mount said cutter blade thereon; and (c) a leaf spring member supported by said slider to come into and out of engagement with said engaging recesses;

wherein (i) said slider includes a body member, a boss member, an operation member supported movably on said body member, and a leaf spring member;

(ii) said leaf spring member includes leg portions expanded obliquely, a protruding portion of an isosceles trapezoid formed at the center portion of said leg portions and capable of engaging with said engaging recesses, and a wide portion formed at a base of said protruding portion and made wider than said obliquely expanded leg portions;

(iii) said body member includes a center recess, an opening formed at the center in the upper face of said center recess for allowing the protruding portion of said leaf spring to go into and out of it, and a boss positioned in the vicinity of said opening for preventing the deformation of the protruding portion of said leaf spring;

(iv) said operation member includes a movable stopper for engaging with said wide portion of the leaf spring to prevent the protruding portion of said leaf spring from moving backward when the leaf spring deflects, and an engaging groove for pushing downward said protruding portion against the elasticity of said leaf spring by the moving operation of said operation member so that the protruding portion of said leaf spring may be released from said engaging recesses.

4. The apparatus of claim 3 wherein the holder is a constructed from a molding of synthetic resin.

5. The apparatus of claim 3 wherein the angle of inclination of the sides corresponding to the legs of the isosceles trapezoids is between about 50 to 85 degrees.

6. The apparatus of claim 3 wherein the angle of inclination of the sides corresponding to the legs of the isosceles trapezoids is between about 50 to 60 degrees.

7. The apparatus of claim 3 wherein the angle of inclination of the sides corresponding to the legs of the isosceles trapezoids is between about 60 to 70 degrees.

8. The apparatus of claim 3 wherein the angle of inclination of the sides corresponding to the legs of the isosceles trapezoids is between about 70 to 85 degrees.

* * * * *